United States Patent [19]

Brown, deceased et al.

[11] 3,972,889

[45] Aug. 3, 1976

[54] FUNGICIDAL N-POLYHALOVINYLTHIOFORMAMIDES

[75] Inventors: Melancthon S. Brown, deceased, late of Berkeley, Calif., by Gustave Kohn, administrator, Berkeley, Calif.

[73] Assignee: Chevron Research Company, San Francisco, Calif.

[22] Filed: Apr. 18, 1975

[21] Appl. No.: 569,517

Related U.S. Application Data

[60] Division of Ser. No. 386,270, Aug. 6, 1972, Pat. No. 3,888,992, which is a division of Ser. No. 253,643, May 15, 1972, Pat. No. 3,771,991, which is a division of Ser. No. 33,878, April 29, 1970, Pat. No. 3,697,571, which is a continuation-in-part of Ser. Nos. 810,368, March 25, 1969, abandoned, and Ser. No. 748,642, June 30, 1968, abandoned, which is a continuation-in-part of Ser. No. 704,555, Feb. 12, 1968, abandoned, said Ser. No. 810,368, is a continuation-in-part of Ser. No. 748,642, , and Ser. No. 764,555.

[52] U.S. Cl. ................................. 424/298; 424/320
[51] Int. Cl.² ........................ A01N 9/00; A01N 9/20
[58] Field of Search ............................ 424/298, 320

[56] References Cited
UNITED STATES PATENTS

| | | | |
|---|---|---|---|
| 3,178,447 | 4/1965 | Kohn | 424/273 |
| 3,344,153 | 9/1967 | Kuhle et al. | 260/453 |
| 3,697,571 | 10/1972 | Brown | 424/298 |
| 3,888,992 | 6/1975 | Brown | 424/298 |

*Primary Examiner*—Leonard Schenkman
*Attorney, Agent, or Firm*—George F. Magdeburger; Dix A. Newell; Raymond Owyang

[57] ABSTRACT

N-polyhalovinylthioformamides of the formula:

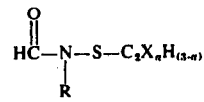

wherein R is hydrogen or alkyl of 1 to 4 carbon atoms, X is halogen of atomic number 17 to 35 and a is 2 or 3. These formamides are fungicidal, algicidal and nematocidal.

5 Claims, No Drawings

FUNGICIDAL N-POLYHALOVINYLTHIOFORMAMIDES

CROSS REFERENCE TO RELATED APPLICATIONS

This application is a division of application Ser. No. 386,270, filed Aug. 6, 1972, now U.S. Pat. No. 3,888,992; which is a division of application Ser. No. 253,643, filed May 15, 1972, now U.S. Pat. No. 3,771,991; which in turn is a division of application Ser. No. 33,878, filed Apr. 29, 1970, now U.S. Pat. No. 3,697,571, which in turn is a continuation-in-part of application Ser. No. 810,363, filed Mar. 25, 1969, now abandoned, and application Ser. No. 743,642, filed June 30, 1968, now abandoned. Application Ser. No. 810,368 is a continuation-in-part of application Ser. No. 748,642 and application Ser. No. 704,555, filed Feb. 12, 1968, now abandoned. Application Ser. No. 748,642 is a continuation-in-part of application Ser. No. 704,555.

FIELD OF THE INVENTION

This invention concerns N-polyhalovinylthioformamides and their use as pesticides, especially as nematocides.

INVENTION DESCRIPTION

The novel formamides of the present invention may be represented by the formula:

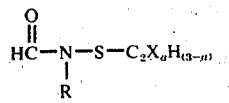

wherein R is hydrogen or alkyl of 1 to 4 carbon atoms, X is halogen of atomic number 17 to 35 and $a$ is 2 or 3. Preferably X is chlorine and $a$ is 3 and R is hydrogen.

Representing polyhalovinyl groups which $-C_2X_aH_{(3-a)}$ may represent are trichlorovinyl, 1,2-dichlorovinyl, 2,2-dichlorovinyl, tribromovinyl, 2,2-dibromovinyl, 1,2-dibromovinyl, 2-bromo-2-chlorovinyl and the like.

Alkyl radicals which R may represent include methyl, ethyl, n-propyl, isopropyl, n-butyl, and isobutyl. The preferred alkyl groups are methyl and ethyl and more preferably methyl.

Typical formamides represented by the above formula are N-trichlorovinylthioformamide, N-tribromovinylthioformamide, N-2,2-dichlorovinylthioformamide, N-2,2-dibromovinylthioformamide, N-1,2-dichlorovinylthioformamide, N-methyl-N-trichlorovinylthioformamide, N-ethyl-N-trichlorovinylthioformamide, N-ethyl-N-tribromovinylthioformamide, N-propyl-N-1,2-dibromovinylthioformamide, and N-butyl-N-1-chloro-2-bromovinylthioformamide.

The formamides of this invention may be prepared by reacting a sulfenyl halide with a primary formamide. This reaction is illustrated by the following chemical equation:

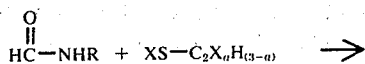

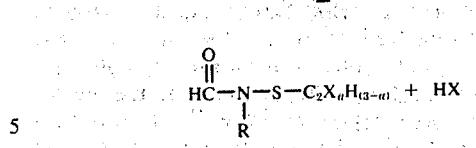

where R, X and $a$ are as previously defined. It is desirable to carry out this reaction in the presence of inert solvents such as dimethyl sulfoxide, dimethylformamide, acetonitrile, dioxane and the like. The reaction temperature is, in general, not critical and will usually be in the range of about −20 to about 50°C., preferably about 0° to 20°C. Likewise, the pressure is not critical and will usually be atmospheric or autogeneous. It is desirable to use stoichiometric proportions of the reactants or a slight excess of the sulfenyl halide reactant.

Formamides of this invention may also be prepared by dehydrohalogenating corresponding N-polyhaloalkylthioformamides. For instance, N-(tetrachloroethylthio) formamides may be dehydrochlorinated to produce N-trichlorovinylthioformamides. This dehydrohalogenation will normally be carried out at low temperatures, usually about 0° to 40°C. and in the presence of solvents such as benzene, toluene, ether, methylene chloride, acetonitrile and chloroform. Mild dehydrohalogenating agents such as tertiary amines (trialkyl amines, pyridine, etc.) or alkali metal carbonates will normally be employed. Triethylamine is a preferred agent.

EXAMPLES

The following examples describe methods which may be used to prepare the formamides of this invention. These examples are not intended to limit the invention described herein. Percentages are by weight.

EXAMPLE 1

15 g. of formamide and 100 ml. of dimethylformamide were placed in a vessel and cooled in an ice bath. 25 g. of trichlorovinylsulfenyl chloride was slowly added to the mixture. After this addition the vessel was removed from the ice bath and allowed to stand for one hour at ambient temperature with stirring. 750 ml. of ice water was then added to the vessel causing a precipitate to form. The precipitate was extracted in ethyl ether and washed with a sodium chloride solution, dried and then stripped. The solid was then dissolved in 50 ml. of hot hexane plus 35 ml. of hot benzene. The hexane-benzene solution was then cooled. The resulting solid product was filtered, washed in petroleum ether and dried. Chemical analysis of the N-trichlorovinylthioformamide was as follows:

|   |   | Calculated | Found |
|---|---|---|---|
| S | % | 15.45 | 15.30 |
| Cl | % | 51.2 | 50.15 |

EXAMPLE 2

15 g. of N-(1,1,2,2-tetrachlorethylthio) formamide and 150 ml. acetonitrile were placed in a vessel cooled in an ice bath. 7 g. of triethylamine in 20 ml. acetonitrile was added dropwise to the vessel. After the addition was complete, the ice bath was removed and the reaction mixture at ambient temperature for 2 hours. The mixture was then cooled and filtered. The acetonitrile was stripped from this filtrate and the stripped product was dissolved in about 500 ml. methylene chloride. This solution was washed with cold water and dried over MgSO$_4$. It was then filtered and the methylene chloride was stripped from the filtrate leaving a solid crystalline residue. This residue was recrystallized twice from a mixture of hexane and benzene to give a small amount of N-trichlorovinylthioformamide. This compound was observed as a solid melting at 50°–53°C. Its S and Cl analyses were:

|   |   | Calculated | Found |
|---|---|---|---|
| S | % | 15.45 | 15.55 |
| Cl | % | 51.2 | 50.40 |

Other formamides of this invention were prepared by the method described in Example 1. These formamides are listed in Table 1.

TABLE I

| Compound | Element Analyses — % | | | | Melting Point °C |
|---|---|---|---|---|---|
|  | S | | Cl | | |
|  | Calculated | Found | Calculated | Found | |
| N-2,2-dichlorovinylthioformamide | 18.60 | 18.12 | 41.30 | 40.40 | 64–77 |
| N-methyl-N-trichlorovinylthioformamide | 14.51 | 15.45 | 48.02 | 47.30 | oil |

TABLE II

| Compound | Nematocidal Activity — % |
|---|---|
| N-trichlorovinylthioformamide | 100 |
| N-methyl-N-trichlorovinylthioformamide | 96 |
| N-2,2-dichlorovinylthioformamide | 100 |
| N-trichloromethylthioformamide | 2 |
| N-1,1,2,2-tetrachloroethylthioformamide | 8 |

As illustrated above, the formamides of this invention may be used to control plant-parasitic nematodes by exposing them to a toxic amount of the formamide. Thus, these formamides will normally be applied to nematode-infested soil at dosages in the range of 3 to 40 lbs. per acre. They may be applied as liquid formulations by spraying or injection. The liquid formulations of these formamides may be solutions, dispersions, or emulsions. Typical solvents which may be used are aromatics such as xylene, toluene and benzene, ketones

UTILITY

The N-polyhalovinylthioformamides of this invention have exhibited biological activity against a variety of organisms, particularly fungi, algae and nematodes. Their activities against nematodes were unexpectedly better than those of the most closely related known formamides, the N-polyhaloalkylthioformamides. Also, many of them were significantly better fungicides and algicides than the known formamides.

The nematocidal activities of the formamides of this invention and their superiority over corresponding N-polyhaloalkylthio compounds were illustrated by testing representative amides of this invention and representative N-polyhaloalkylthio compounds by the following method.

A 0.38 ml. portion of a 3% acetone solution of the test compound was diluted with 1 ml. acetone. The resulting solution was homogeneously mixed with 20 cc. of vermiculite. The treated vermiculite was then mixed homogeneously with 750 g. of soil, dry weight basis, which was severely infested with free-living nematodes (mixed culture of *Meloidogyne javanica* and *Meloidogyne incognita*). This mixing gave a concentration of approximately 15 parts of the test compound per million parts of soil. This treated oil was stored for 4 days at 65°–75°F. It was then divided equally into 3 parts, each of which was put into a separate pot and kept for another 3 days. A 3-week old tomato (v. Bonny Best) seedling was then transplanted into each pot and incubated for 13 days under greenhouse conditions. After this period they were removed and the soil was washed from their roots. The nematocidal effectiveness of the test compound was determined by observing each plant for signs of nematode invasion (number of galls formed, stunting, etc.).

The results of these tests, reported as the average of the 3 replicates on a 0 to 100 basis — 0 indicating no effectiveness; 100 indicating complete effectiveness — are reported in Table II.

such as cyclohexanone and the like. These liquid formulations will usually contain a wetting agent to facilitate the formamide's penetration into the soil and generally enhance its effectiveness. They may also be applied as solid formulations containing carriers such as soil, sawdust, clay and the like. When used as a solid, these formamides will usually be plowed into the soil. Following their application to the soil, the soil will be watered to disperse the formamide below ground level.

Formamides of this invention are particularly useful for controlling organisms such as algae, bacteria, molds and occasionally aquatic weeds which foul aqueous industrial effluents and cooling streams, such as those occurring in the paper and food processing industries. They may also be used to control such organisms in other aqueous bodies such as lakes, streams, canals, pools and the like. When so used, a biocidal quantity of one or more of the formamides of this invention is added to the aqueous growth environment of the organisms. Usually, this dosage will range between about 0.1 and 50 ppm. In any given instance, the optimum dosage will depend upon the particular organism and aqueous body involved. For instance, when used to control algae, these formamides will usually be employed at concentrations of about 0.1 to 10 ppm. In terms of pounds of formamide per acre of water one foot deep 0.1 to 10 ppm is equal to about 0.3 to 30 lbs. per acre of water one foot deep. These formamides may be applied to the aqueous growth environments of such organisms as dispersible powders or in solution with water-miscible solvents.

Representative formamides of this invention were tested as algicides by the following method.

An acetone solution of equal parts of formamide and a surfactant was prepared. This solution was mixed with a nutrient broth in a quantity sufficient to give a concentration of 2 ppm formamide. Four repliace 150 ml. specimen cups were filled with this mixture. 350–400 mg. of Euglena was added to each specimen cup and then cups were then placed in an environment chamber for incubation. The cups were observed periodically for algae growth. The algicidal effectiveness of the formamide was determined based on a final observation of algae growth after 10 days.

The results of these tests, reported as the average of the 4 replicates on a 0 to 100 basis — 0 indicating no effectiveness; 100 indicating complete effectiveness — are reported in Table III.

TABLE III

| Compound | Algicidal Effectiveness |
| --- | --- |
| N-trichlorovinylthioformamide | 100 |
| N-methyl-N-trichlorovinylthioformamide | 100 |
| N-2,2-dichlorovinylthioformamide | 100 |

Comparative algicidal testing indicated the formamides of this invention were more effective than corresponding N-polyhaloalkylthioformamides.

Formamides of this invention were also used to control fungi such as *Pythium ultimum*, *Rhizoctonia solani*, *Fusarium oxysporum*, *f. phaseoli*, *Helminthosporium sativum*, *Verticillium alboatrum*, *Monilinia fructiocola* and *Alternaria solani*. When used as fungicides, the formamides of this invention will be formulated and applied in fungicidal amounts by conventional art methods to fungi or hosts which are subject to fungus attack, especially vegetative hosts such as plants, plant seeds, paper and the like. They may be combined with inert liquids and solid carriers as powders, solutions or dispersions for such use.

Pesticidal formulations of the formamides of this invention may also contain stabilizers, spreading agents, sticking agents, fillers, other compatible pesticides and the like.

As will be evident to those skilled in the art, various modifications on this invention can be made or followed, in the light of the foregoing disclosure and discussion, without departing from the spirit or scope of the disclosure or from the scope of the following claims.

I claim:

1. A method for controlling fungi which comprises contacting said fungi or their hosts with a fungicidally effective amount of a polyhalovinylthioformamide of the formula

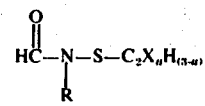

wherein R is hydrogen or alkyl of 1 to 4 carbon atoms, X is halogen of atomic number 17 to 35 and $a$ is 2 or 3.

2. The method of claim 1 wherein R is hydrogen, methyl or ethyl.

3. The method of claim 1, wherein R is hydrogen.

4. The method of claim 1 wherein R is hydrogen, X is chlorine and $a$ is 3.

5. The method of claim 2 wherein X is chlorine and $a$ is 3.

* * * * *